United States Patent [19]

Murray

[11] Patent Number: 4,582,699

[45] Date of Patent: Apr. 15, 1986

[54] ASSAY OF IMMUNOGLOBULIN A PROTEASE AND THE RAPID DIAGNOSIS OF GONORRHEA

[75] Inventor: Kittie A. Murray, New York, N.Y.

[73] Assignee: Magbon Test Company, Great Neck, N.Y.

[21] Appl. No.: 333,713

[22] Filed: Dec. 23, 1981

[51] Int. Cl.[4] ...................... G01N 33/54; A61K 39/40
[52] U.S. Cl. ....................................... 424/1.1; 424/87;
424/9; 435/7; 435/23; 435/259; 435/810;
436/511; 436/515; 436/518; 436/533; 436/536;
436/540; 436/542; 260/112 R; 206/569
[58] Field of Search ...................... 424/1.1, 1.5, 12, 87,
424/177; 23/230 B; 435/4, 7, 23, 871, 882, 851,
259, 810; 436/511, 518, 536, 548, 63, 86, 804,
808, 515, 533, 540, 542; 422/61; 260/112 R;
206/569

[56] References Cited

PUBLICATIONS

Mulks, M. H. et al., New England Journal of Medicine, vol. 299, (18), pp. 973–976 (1978).
Plaut, A. G. et al., New England Journal of Medicine, vol. 298 (26), pp. 1459–1463 (1978).
Blake, M. S. et al., Infection and Immunity, vol. 22 (2), pp. 350–358 (1978).
Mulks, M. H. et al., J. Experimental Medicine, vol. 152, pp. 1442–1447 (11-1980).
Kilian, M. et al., J. Immunology, vol. 124 (6), pp. 2596–2600 (1980).
Kilian, M. et al., Infection and Immunity, vol. 26 (1), pp. 143–149 (1979).
Jabib, R. S. et al., Biochimica et Biophysica Acta, vol. 526, pp. 547–559 (1978).
Mulks, M. H. et al., J. Infectious Disease, vol. 141, (4), pp. 450–456 (1980).
Male, C. J., Infection and Immunity, vol. 26, pp. 254–261 (1979).
Blake, M. et al., J. Infectious Diseases, vol. 139, (1), pp. 89–92 (1979).
Kilian, M. et al., Infection and Immunity, vol. 31 (3), pp. 868–873 (3-1981).

*Primary Examiner*—Ben R. Padgett
*Assistant Examiner*—M. Moskowitz
*Attorney, Agent, or Firm*—Ostrolenk, Faber, Gerb & Soffen

[57] ABSTRACT

A method for rapid diagnosis of gonorrhea is set forth comprising assay of the enzyme immunoglobulin A protease (IgAP). Immunoassays including radioimmunoassay and enzyme-linked immunoassay with monoclonal antibodies to IgAP are disclosed. A kit for early detection of gonorrhea is given. The assay and kit of the present invention may also be used in the detection of meningitis.

31 Claims, No Drawings

ASSAY OF IMMUNOGLOBULIN A PROTEASE AND THE RAPID DIAGNOSIS OF GONORRHEA

BACKGROUND OF THE INVENTION

Gonorrhea is a sexually transmitted disease caused by the bacterium *Neisseria gonorrhea*. The disease has plagued mankind since ancient history, and although penicillin and related "miracle drugs" have helped control the spread of gonorrhea, it still persists in epidemic proportions. In the United States along 3 million cases of gonorrhea are reported annually and worldwide over 60 million cases are reported each year.

A major reason for the rampant spread of gonorrhea is the lack of a rapid method for detection of infection in its early stages. *Neisseria gonorrhea* may thrive on the genital membranes several days before the obvious symptoms of prurulent discharge become visible, and during this period contact with a non-carrier may result in unwitting transmission of the bacterium. Moreover, many carriers of the disease, especially women, are asymptotic and spread the disease unknowingly.

Current diagnostic methods for gonorrhea include preliminary microscopic observation by a trained clinician of gram-stained extract from uro-genital membranes followed by incubation of extract on a medium selective by *Neisseria gonorrhea*. Final chemical tests are made in the laboratory and finally reported to the patient who may then be treated. This diagnostic procedure is a time-consuming process requiring trained personnel and sophisticated instrumentation.

SUMMARY OF THE INVENTION

Accordingly, it is the object of the present invention to provide a simple, rapid method for diagnosis of gonorrhea.

It is a major object of the invention to provide a method for diagnosis of gonorrhea which may be used by a doctor in his office in conjunction with treatment of the disease.

It is an important object of the present invention to provide a method for diagnosis of gonorrhea which can be used to screen large numbers of samples for possible infection.

It is a further object of the present invention to provide a kit for use in self-detection of gonorrhea.

Other objects of the invention will become apparent from the following description.

The present invention comprises diagnostic reagents and techniques recently made available by advances in the fields of molecular biology and genetic engineering.

More particularly, the diagnosis technique of the present invention comprises a detection method for immunoglobulin A protease, (IgAP), an enzyme produced almost exclusively by *Neisseria gonorrhea*. The diagnostic method utilizes the antibody to IgAP preferably the mono clonal antibody. This monoclonal antibody may detect IgAP in samples of urogenital membranes using known techniques of immunology including enzyme-linked immunoassay (ELIZA), biligand binding (sandwich technique), radialimmunodiffusion, radioimmunoassay (RIA) and agglutination. The antibody may also be used to isolate and purify IgAP from biological samples where competing enzymes are present after which analysis of IgAP by reaction with appropriately tagged substrate is possible.

The antibody to IgAP in certain embodiments of the diagnostic method of the present invention may be immobilized on an inert surface, embedded in a gel, or may be conjugated to a molecule which imparts color, fluorescense or radioactivity to the antibody.

Certain embodiments of the present invention may employ substrate, preferably immunoglobulin A, subclass 1, or a synthetic polypeptide which is conjugated to a chromophoric or radioactive agent. Reaction between IgAP isolated by means of the antibody and substrate is measured by loss of color or radioactivity in substrate or production of color or radioactivity in products. Dialysis tubing, filter aids, or electrophoresis may be used to separate products from reactants. Alternatively, substrate may be immobilized on an inert surface and reaction with IgAP may be observed as separate bands of color or radioactivity on the inert surface.

Biological samples which may be analyzed by the method of the present invention can be obtained via swabs, tampons or vaginal washes in the case of women and urine or penal or rectal smears in the case of men. Cultured samples of *Neisseria gonorrhea* from these or other biological sources may also be used. The samples may be analyzed directly or may be lyzed and/or concentrated.

The reagents and means of diagnosis of the present invention may be embodied in a kit for use by a doctor during examination of a patient in the office or may be adapted and automated for analyzing large numbers of samples at a central receiving center such as an Army induction center, a college campus or a veneral disease clinic.

A preferred embodiment of the present invention comprises a kit for self-diagnosis of gonorrhea by individuals. The kit of this embodiment comprises a sample collection device, the antibody to IgAP and means for detecting reaction between antibody and IgAP in the samples. Suitable buffering agents and ionic salts may also be included in the kit.

The method and means of the present invention may also be adapted for preliminary diagnosis of meningitis, a disease caused by *Neisseria meningitidis* which also produces IgAP. Biological samples suitable for analysis include spinal fluid and synovial fluid as well as extracts of uro-genital membranes.

Detailed Description of the Invention

A method and means for detection of the bacteria *Neisseria gonorrhea*, *Neisseria meningitidis*, *Haemophilus influenza*, *Streptococcus pneumonia*, and other bacteria which elaborate the enzyme IgAP comprising immunoassay of IgAP is hereinafter set forth.

Immunochemical assays of IgAP may employ the whole anti-serum to IgAP, the globulin fraction, or the purified antibody specific for IgAP including the monoclonal antibody under conditions of pH, ionic strength, temperature and concentrations which are conducive to formation of the IgAP-antibody complex.

The anti-serum to IgAP may be produced in a host animal such as rabbit or sheep. The serum fraction containing the antibody may be isolated by standard techniques. This anti-serum may be employed in several of the embodiments of the invention hereinafter set forth, or the serum may be further purified by electrophoresis, high speed centrifugation or the like to produce a more sensitive and specific antibody. Ultimately, large quantities of the highly specific monoclonol antibody may be produced by means of the hybrid-myeloma technique by methods known to those skilled in the art.

Certain embodiments of the present invention employ the antibody to IgAP immobilized on cellulose, agarose, sephadex or glass beads or other similar inert surfaces such as metal, plastic or ceramic which do not interfere with subsequent reaction. Adsorption, Br-CN activation or other techniques known in the art may be employed to immobilize the antibody.

Other embodiments of the present invention employ the antibody to IgAP conjugated to a chromophoric (highly colored) molecule, an enzochromic (an enzyme which produces color upon addition of reagents) molecule, fluorochromic (fluorescent) molecule or a luminogenic (luminescent) molecule. Chromophoric molecules which may be used are 2,3-dinitrobenzene (DNB) salts, dinitrophenol (DNP) and methyl and butyl orange. Other suitable chromophoric agents are well-known in the art. Enzochromic molecules which may be conjugated with the antibody are enzymes which give color with appropriate reagents. Examples are alkaline phosphatase (ALP) which develops color with nitrophenyl phosphate (NPP), glucose oxidase with glucose, and D-galactopyranoside. These and other examples are well-known in the art. Examples of fluorogenic agents are 2,4-dinitrofluorobenzene and "pipsyl" derivatives. Luminogenic molecules may be conjugated to antibodies by the method of Branchini, et al. (*Biochem. Biophys. Res. Commun.* 97, 334 [1980]). The term "Chromophoric" hereinafter is intended to include "enzochromic", "fluorochromic" and "luminogenic" molecules as well.

The present invention in certain embodiments comprises in addition substrate to IgAP, namely $IgA_1$ or a suitable polypeptide containing the requisite prolinethreonine bond. These substrates may likewise be conjugated to chromophoric molecules and/or immobilized on an inert surface. Substrate IgAhd 1 may be prepared by the monoclonal technique after isolation from a biological source such as colostrum, preferably human colostrum. $IgA_1$ may be assayed during monoclonal production by means of IgAP utilizing such techniques as enzyme-linked immunoassay, radioimmunoassay, precipitin reaction or radialimmunodiffusion using electrophoresis when necessary.

Certain embodiments of the invention also utilize IgAP tagged with a radioactive element. $I^{125}$ conjugated by means of the chloramine-T procedure is a common example but other methods known in the art may also be employed.

A. Bidentate Ligand Binding—"Sandwich" Technique

IgAP is a large molecule with more than one antigenic site, i.e., it is bidentate which is the basis of the following immunoassay of IgAP wherein the immobilized antibody to IgAP, preferably on an inert surface such as paper or a similar bibulous mat, is put into contact with a sample suspected of containing IgAP. In the case of aqueous samples such as vaginal washings or urine, the solution is buffered and ionic salts may be present at optimum concentration for IgAP-antibody interaction. TRIS or borate buffered phosphate at pH 7.5 to 9.0 and ionic strength about 0.010 to 0.5, for example, are suitable buffering agents and ionic salts. This "sandwich method" may also be used directly on a tampon-sample surface and in this case buffers and salts may be included on the inert surface along with antibody. The inert surface with antibody or antibody-IgAP complex thereon is next put into contact with antibody to IgAP conjugated to a chromophoric molecule. Preferably the antibody is in solution buffered at pH from about 7.5 to 9.0 and ionic concentration equivalent to about 0.01M to about 0.1M NaCl. After careful rinsing under water or with suitable surfactants such as Tween 20 to remove excess colored antibody, the inert surface is inspected for color, fluorescence or luminescence directly or after addition of color-developing agents. Color on the inert surface indicates interaction between immobilized IgAP-antibody IgAP complex and conjugated antibody in solution. A control may be run for color comparison.

This "sandwich technique" may be adapted to clinical use by employing antibodies tagged with radioactive elements and observing either depletion of activity in solution or uptake on solid support of radioactivity. This embodiment is highly sensitive and rapid and suitable for large numbers of samples.

B. Enzyme-Linked Immunoassay—ELIZA

A solution comprising IgAP conjugated to enzyme which forms color with developing reagents and buffer and ionic salts suitable for reaction between IgAP and the antibody to IgAP is put into contact and allowed to react with antibody immobilized, preferably, on an inert surface such as a paper strip or on glass beads. The amount of enzochromic conjugated IgAP is sufficient to saturate about 50% of the reactive sites on the immobilized antibody. The inert surface with antibody-IgAP-enzyme complex is put into contact with buffered sample suspected of containing *Neisseria gonorrhea* or other bacteria which elaborate IgAP, said sample having an unknown amount of IgAP. The color of the resultant immobilized antibody-IgAP-enzyme complex on the strip after color developing reagents are added is observed in comparison to a control strip which has not been treated with sample containing IgAP. Dilution in color on inert surface treated with sample means presence of IgAP in the unknown sample.

This method may be adapted for clinical use by contacting samples and immobilized enzyme, preferably in tubes which may be centrifuged and watching developing color spectro photometrically. This embodiment is very sensitive and rapid.

C. Radialimmunodiffusion—Precipitin reaction

The monospecific antibody, preferably the monoclonal antibody to IgAP is suspended in a softened gelatinous medium such as agar or agarose along with buffers and salts to maintain pH between about 6.0 to 9.0 and ionic strength between about 0.01M to 0.5M for optiman antigen-antibody interaction. The suspending medium of U.S. Pat. No. 4,259,207 is a suitable example. The mixture is spread out to harden on a test plate or, preferably, poured into a disc-shaped container such as an Octolony plate. A small amount of sample is placed on the solidified gel, preferably in a center well and the plate or disc is allowed to stand preferably covered for a period of hours. Diffusion of sample into the surrounding area occurs during this period. If the antigen IgAP is present, it reacts with the embedded antibody and causes an opaque area in a radial pattern about the point of application of sample. A control can be run for comparison. Calibration of an amount of IgAP in sample, if desired, can be obtained by controlling temperature, time and size of sample and comparing the resultant size of radial area with one of known concentration.

In other embodiments, crude antiserum or partially purified antibody therefrom may be likewise embedded in the agar. Lysing of sensitized cells may also be observed.

D. Radioimmunoassay

The antibody to IgAP is immobilized on an inert surface such as glass beads in a separation column. A portion of IgAP is conjugated to a radioactive element, preferably $I^{125}$ and allowed to react with the immobilized antibody in an amount sufficient to saturate 50% of the binding sites. The immobilized antibody-enzyme complex is put into contact with a sample suspected of containing IgAP, the sample being buffered between pH 6-9 and containing total ionic salts about 0.05 to 0.5M for optimal reaction conditions for formation of IgAP-antibody complex. The IgAP is eluted from the antibody and the eluant is measured for radioactivity. Loss of activity compared to a control indicates IgAP in sample.

E. Haemagglutination

IgAP may be assayed through standard haemagglutination techniques with antiserum to IgAP used as sensitizing agent.

F. Assays of IgAP Based on Proteolytic Reaction with Substrate

IgAP is a proteolytic enzyme which catalyzes the hydrolysis of substrate to smaller fragments. Thus $IgA_1$ is hydrolyzed to the smaller $F_{ab}$ and $F_c$ fragments.

$IgA_1$ may be isolated from colostrum or the plasma of patients with multiple myeloma or Waldenstroms macroglobulinemia by methods known in the art (Mesticky et al., *J. Lab. Clin. Med.* 89, 919 [1977]). $IgA_1$ may be purified on DEAE cellulose and otherwise treated to remove $F_{ab}$ and $F_c$ fragments, passing it through columns of immobolized antibodies specific for the fragments, by electrophoresis or by other methods known in the art. $IgA_1$ in highly purified, specific form may be produced by the monoclonal antibody technique using the methods of the hybrid-myeloma techniques well known to those skilled in the art.

$IgA_1$ is the only known naturally occuring substrate of IgAP, but a polypeptide with the characteristic prolyl-threolyl link which is the receptor site for the enzyme may be synthesized for the purpose of assay. The term "substrate" hereinafter refers to both $IgA_1$ and such synthetic polypeptides which may serve as substrates to IgAP.

The presence of IgAP may be demonstrated by hydrolysis of substrate as evidenced by production of characteristic products or by loss of substrate itself. The proteolytic reaction proceeds most favorably in a solution (hereinafter referred to as "reaction solution"): comprised of buffer, preferably 0.05M phosphate buffer, pH 7.5 with 0.85% NaCl (PBS) at room temperature for a period of up to three hours. TRIS (Hydroxymethylaminomethane), 0.05M, pH 8.1 is also a suitable buffer. A heavy metal may be present in reaction solution.

Prior to assay, sample may be treated to concentrate IgAP and to separate it from interfering proteases by contacting solution with antibody to IgAP immobilized on an inert surface such as glass beads or a paper strip in a buffered solution at pH 8-10. The inert surface with IgAP-antibody complex thereon is rinsed and then put into contact with substrate to IgAP. Alternatively, IgAP may be eluted from the IgAP-antibody complex by a solution at lower pH—about pH 6.5, for instance, prior to treatment with substrate.

The following methods are assays based on the proteolytic reaction of IgAP.

1. Colorimetric Assays of Chromogenic Substrate

A preferred assay of IgAP comprises the colorimetric detection of the reaction between IgAP and substrate. The substrate is conjugated to a chromogenic molecule by methods described hereinabove. Color in smaller cleavage products indicates reaction between substrate and IgAP. In this assay, products must be separated from reaction solution to locate color transfer. This separation may be based upon size differences between products and reactants. $IgA_1$, for instance, is of molecular weight about 120,000 whereas the smaller cleavage fragments $F_{ab}$ and $F_c$ are in the range of 30,000 daltons.

In a preferred embodiment of the present invention, conjugated substrate at concentration of about 5 mg/ml and a sample suspected of containing IgAP are incubated up to three hours in reaction solution. Conjugated substrate and sample are enclosed during this incubation in dialysis tubing which is of pore size sufficient to prevent passage of the larger substrate but permits egress of smaller reaction products. The dialysis tubing is then suspended in a second portion of the same reactant solution. Development of color in the suspending reaction solution and loss of color within the dialysis tubing indicate reaction between IgAP and substrate.

Another embodiment utilizes a column of beads of controlled diameter to separate products from reaction solution by means of molecular weight.

In embodiments adapted for clinical use, electrophoretic separation techniques such as isoelectric focusing or zone electrophoresis which are based on differences of both size and charge distribution between products and reactants may likewise be used to separate products from reactants. Products separated electrophoretically may be detected by characteristic locations compared to standards or may be identified by color or immunochemically. Resinous beads of charged surfaces may also be used to separate products and reactants.

Another preferred embodiment comprises chromophoric $IgA_1$ immobilized at a defined area of an inert surface such as paper or a similar bibulous mat. This surface is put into contact with reactant solution containing suspected IgAP and after a period of time the paper is inspected for movement of color. A band of color separate from the main band at the initial location indicates proteolysis of conjugated substrate by IgAP. A suitable control for comparison comprises immobilized chromogenic $IgA_2$ which is resistant to IgAP. An electrical field may be applied to enhance separation of reactant and products and color developing reagents may be applied to locate movement of products on the strip. Alternatively, reagents specific for products may be located upfield from the initial site where they may react with and identify reaction products. In this embodiment, for example, proline oxidase with appropriate buffers and ionic salts may be deposited upfield along with an appropriate chromophoric reagent such as o-aminobenzaldehyde which turns yellow in the presence of 1'-pyrroline-5-carboxylic acid (PCA') (Dendinger and Brill, *J. Biochemistry* 103, 145 [1970]), a product of the reaction between proline oxidase and proline. Color on the paper located upfield thus indicates proline on the terminal end of the fragment produced by IgAP. A control may be run on samples containing no IgAP for color comparison.

In other embodiments for clinical use, the reaction of proline oxidase and terminal proline may be measured spectrophotometrically by addition of o-amino-benzaldehyde or by monitoring an associated NADH coupled enzyme system in solution.

In another embodiment, the reaction strip may be treated with chromogenic antibodies specific for reaction products.

2. Immunoassay of Substrate or Products

Standard immunochemical techniques may be adapted to follow the decrease in concentration of substrate or the increase of concentration of products in reaction solution produced by IgAP in the sample to be analyzed.

A preferred embodiment of the invention comprises measurement of substrate by haemagglutination. An amount of substrate to IgAP is contacted with the sample to be analyzed which is preferably lyzed and in reaction solution. After a period of time, up to 3 hours, a measured amount of solution is added to latex beads which have coated with the antiserum to substrate in bovine serum albumin buffered between pH 9 and 10. The same amount of solution containing no sample as control is added to another portion of coated latex beads. A difference in agglutination rate and amount between sample and control indicates loss of substrate through proteolysis with IgAP. Spectrophotometric observation of the reaction is also possible. The sensitivity of this reaction may be improved by incorporating the antibody in a gel matrix and observing precipitation of enzyme-antibody complex as a single line or as a radiation area. Rough quantification is achieved by controlling concentrations of antibody.

For assay of proteolytic reaction between substrate and IgAP, antibodies to products of reaction may be used to sensitize the latex beads. A positive test is agglutination of precipitation compared to a control with no sample. An antibody specific for terminal proline or threonine may be used to coat the latex beads or, when $IgA_1$ is used as substrate, the antibodies to $F_{ab}$ and $F_c$.

In another embodiment of the present invention, substrate is immobilized on an inert surface. The surface with substrate is put into contact with a sample in reaction solution and after a period of time, up to 3 hours, the surface is removed, rinsed and put into contact with a solution containing antibody to substrate, said antibody being tagged with a colored molecule. After rinsing, the surface is inspected for color. Color indicates reaction between colored antibody and immobilized substrate. Lack of color indicates loss of substrate by reaction with IgAP. A control may be run for color comparison.

Alternatively, the immobilized substrate after contact with reaction solution may be put into contact with color conjugated antibodies specific for the fragment remaining on the inert surface. In this method color adhering to the inert surface indicates reaction of the IgAP and substrate.

Likewise, the immobilized substrate after contact with reaction solution may be put into contact with a substance specific for the terminal proline or threonine end of hydrolyzed substrate. The substrate may be a chromophoric antibody specific for this terminal group or it may be prolinase and a chromophore which turn color in the presence of the terminal proline. Prolinase and chromophore may be in solution or may be immobilized on a second inert surface.

Other immunoassays including radialimmunodiffusion, RIA or ELIZA as described hereinabove may be used to detect loss of substrate and products of reaction.

It is to be understood that methods described hereinabove for assay of IgAP employing colored reagents have been presented most specifically for application where neither trained personnel nor sophisticated instruments are available. These methods, however, may be adapted for use in a clinical setting where large numbers of samples are to be assayed by substituting redioactive elements for chromogenic conjugated molecules. Thus the assay by proeiolytic reaction can be followed as the transfer of radioactivity from substrate to product as measured by scintillation counters, Geiger counters or other instruments capable of measuring radioactive decay.

It is also to be understood that the term "color" is not to be interpreted as being limited to the narrow visible range of the electromagnetic spectrum, but is meant to include wavelengths which may be measured by standard spectrophotographic instruments such as spectrophotometers and absorption and emission colorimeters in both the uv and the ir range.

Although it is contemplated that the methods of the present invention are to be applied to biological fluids themselves, the sensitivity and specificity of the method can be improved by culture of the fluids preferably on medium selective for *Neisseria gonorrhea* such as Thayer-Martin, Chocolate-sugar, NYC medium or Transgro medium for 24 hours with an iron source such as Fe-dextran complex (inferon) as taught in U.S. Pat. No. 4,229,530, prior to testing. Samples in clinical settings may be vaginal washings obtained by collecting 10 cc of PBS directed at the cervix in the case of females or may be about the first few cc of urine, in the case of males to be passed. The urine may be centrifuged and the sediment used for analysis, preferably after typing. Vaginal, urethral or rectal swabs may also be employed.

Sensitivity may also be improved by preliminary treatment of biological samples with lysing agents such as isotonic solution, sound, or lysozyme to release IgAP into the extracellular environment. U.S. Pat. No. 4,166,765, for example, discloses suitable lysing procedures for biological samples containing bacteria which elaborate IgAP. Any lysing agent may be employed which does not interfere with subsequent enzyme activity.

III Assays Embodied in Kit Form

The diagnostic method and means of the present invention may be embodied in the form of a kit for use by individuals for self-diagnosis of gonorrhea in the privacy of their homes.

The kit comprises a means for sample collection, the antibody to IgAP and a means for detecting reaction between sample and antibody. The kit may also comprise a substrate to IgAP and reagents for a suitable reaction solution.

The sample collection device, in the case of males, is a vessel marked to receive only the first few milliliters of urine to be passed. These first few milliliters wash out of the urethra the purulent discharge caused by *Neisseria gonorrhea* which contains the highest concentration of IgAP. An early mornng sample is preferable.

Sample collection, in the case of females is a tampon which is to be worn in the vagina close to the cervix for a period of several hours preferably immediately after suspected contact with *Neisseria gonorrhea* after which time it is removed to a receiving vessel where it is either contacted directly with antibody to IgAP or it is extracted with lysing agents and reaction solution in a stoppered tube.

The antibody to IgAP may be immobilized and/or conjugated with a chromophor. IgAP may be complexed to the antibody for use in enzyme linked immunoassay. In embodiments employing the proteolytic action of IgAP, preferably IgA$_1$, optionally conjugated with a chromophoric molecule is included. The substrate may be immobilized on an inert surface such as paper or a similar bibulous mat or on inert beads such as Sepharose or glass. These proteinaceous reagents may be packaged in sterile hermetically sealed packets to prolong shelf life during marketing.

Reagents comprising buffer and ionic salts may be included in the kit as powders in a stoppered vessel. The vessel is marked to indicate the volume to which it is to be filled with water to give the proper dilution of reagents for reaction. Optionally, distilled water may be included in the kit for dilution of reagent solution.

The means for detecting reaction in the case of immunoassay in a preferred embodiment of the invention is a gelatinous medium in which the antibody to IgAP is suspended. The gelatinous medium is in a transparent glass or plastic container and comprises buffer and ionic salts for optimal conditions for formation of the IgAP-antibody complex. Reaction is noted as a transparent area radiating from the central point at which the sample is applied.

The means for detecting reaction in another preferred embodiment comprising immunoassay is the antibody to IgAP conjugated to a chromophore in a sealed, sterile packet along with buffer and ionic salts. For assay, the contents of the packet are diluted with water in a marked tube supplied in the kit. Included also in this embodiment is the antibody to IgAP immobilized on an inert surface. For assay, the inert surface with immobilized IgAP is put into contact with sample and then with the solution of chromophore-conjugated IgAP. The inert surface is inspected for color which indicates gonorrhea.

The means for detection of IgAP in another preferred embodiment comprising enzyme-linked immunoassay (ELIZA) is buffer and ionic salts in a tube which are diluted before use to a marked volume with water. Immobilized antibody to IgAP is coated with IgAP conjugated to a color-forming enzyme so that about 50% of the reactive sites are covered. Sample is introduced into the buffered solution preferably after being lyzed and contacted with the inert surface wtih immobilized antibody-enzyme complex thereon. Color developing agents are added to the inert surface containing the immobilized antibody-enzyme complex. Dilution of color on the inert surface compared to a control indicates IgAP in the sample.

Another embodiment of the kit of the present invention comprises substrate to IgAP immobilized at a discrete area on an inert surface, preferably paper, and conjugated to a chromophoric molecule. In this embodiment, the immobilized antibody to IgAP is contacted with sample, preferably rinsed, and put into contact with immobilized substrate. Movement of the color on the paper in a separate band indicates proteolysis of immobilized substrate by IgAP in sample. The separate band may also be identified by developing agents for enzyme linked to substrate. Alternatively prolinase and o-aminobenzaldehyde may be located at a distance from the original site of substrate immobilization. Fragments of proteolysis migrating to this separate band give the yellow color characteristic of terminal proline.

In another embodiment of the kit of the present invention the immobilized antibody to IgAP is contacted with sample and then added to a reaction solution containing substrate conjugated to a chromphopric molecule in a length of dialysis tubing which is closed at both ends and suspended in a second volume of reaction solution containing no substrate or sample. The dialysis tubing contains pores which allow passage of smaller reaction products but not substrate. Color development in suspending reaction solution indicates reaction by IgAP.

Alternatively the immobilized antibody-IgAP and colored substrate are allowed to react in the tube containing reaction solution and then poured through a column of inert beads of graduated size or resinous beads of charged surfaces which allow passage of smaller fragments but retard passage of the large substrate. Color in eluent indicates reaction of sample with IgAP.

The kit of the present invention may also comprise the antibody to IgAP suspended in a gelatinous medium along with suitable buffering agents and ionic salts to maintain reaction conditions between IgAP and antibody. Sample is applied to a portion of the gelatinantibody and reaction is observed as an opaque area radiating from the spot where sample is applied.

The present invention is illustrated by the following examples. However, it should be understood that the invention is not limited to the specific details of these examples.

EXAMPLE 1

Bidentate ligand binding ("sandwich") technique

A. Preparation of reagents

1. Preparation of antibody to IgAP 30 mg of IgAP harvested from growing cultures of *Neisseria gonorrhea* is injected into rabbits over a period of 3 to 4 weeks. Anti-serum containing antibody to the enzyme is removed from the rabbits and the globulin fraction is prepared by the standard method ammonium sulfate precipitation.

2. Preparation of immobilized antibody to IgAP 250 mg of the globulin fraction diluted to 10 ml in 0.01M borate buffered saline (BBS) with 0.1% bovine serum albumin (BSA) and 0.2% Triton-X-100, pH 7.5 is immobilized by the standard azo-linkage coupling technique to the surface of an inert bibulous mat.

3. Preparation of chromogenic antibody to IgAP 250 mg globulin fraction diluted to 10 ml in 0.01M borate buffered saline (BBS) is added to 10 ml 2,4-dinitrobenzene (0.05M), the solution is centrifuged and the precipitate is washed and re-suspended in 10 ml 0.01 BBS.

D. Preparation of sample

Exudate caused by growth of *N.gon.* which has accumulated on the penis outside the urethral opening is collected on a cotton-tipped wooden splint.

C. Diagnostic test

The wooden splint with urethral exudate is touched to the inert surface with immobilized antibody thereon. The inert surface is dipped into the solution containing chromogenic antibody to IgAP, rinsed by dipping into reagent solution and inspected for color. The presence of color adhering to the inert surface indicates IgAP in the exudate and hence *N.gon.*

EXAMPLE 2

Monoclonal antibody to IgAP: Hybridoma technique

The globulin fraction obtained as described in Example 1 is further refined by electrophoresis. The crude antibody is eluted from the electrophoretic gel and used in the production of the monoclonal antibody by the myeloma hydridoma technique wherein a cell from a stable myeloma cell culture is fused in the presence of polyethylene glycol with IgAP antibody-producing cells from a tumorous mouse. The fused cell is grown by standard cell culture techniques and the antibody to IgAP is harvested therefrom.

This monoclonal antibody is suspended in TRIS buffer, pH 7.5, 0.05M for reaction with antigen IgAP. The monoclonal antibody, for the purpose of various diagnostic methods herein presented, may be immobilized or tagged with a chromogenic molecule or radioactive element by methods described in Examples 1, 3 and 4.

EXAMPLE 3

Detection of *Neisseria gonnorrhea* using IgAP antibody: enzyme-linked immunoassay techique (ELIZA)

A. Preparation of Reagents:

The antibody to IgAP is prepared and immobilized as in Example 1. A second portion of IgAP is conjugated with alkaline phosphatase and suspended in 5 ml 0.05M TRIS buffer. pH 8.5. The inert bibulous mat with antibody immobilized thereon is treated with conjugated IgAP in an amount sufficient to saturate about 50% of the reactive sites.

B. Preparation of sample:

10 ml phosphate buffered saline (PBS) are directed at and collected from the vaginal wall.

C. Diagnostic test

A first inert strip with enzochromic IgAP immobilized thereon is inserted into the vaginal wash sample, removed and added to a solution of p-nitrophenyl phosphate (NPP) (1 mg/ml) in 10% dietnanolamine buffer, pH 8.8 containing 1 mM magnesium chloride. A second control inert NPP. The color of the two strips is compared. Dilution of color on the sample strip compared to control strip indicates the presence of IgAP.

EXAMPLE 4

Automated Screening test for *Neisseria gonorrhea* and *Neisseria memingitidis:* Radioimmunoassay (RIA)

A. Preparation of Reagents:

The antiserum to IgAP is prepared and immobilized as in Example 1. IgAP is tagged with $I^{125}$ by the chloramine T method wherein 0.02 mg IgAP in 0.05 ml 0.5M sodium phosphate buffer, pH 7.5 is added to 1.0 millicuries of $I^{125}$ and 0.01 ml of chloramine T solution (1.25 mg/ml in 0.5 M sodium phosphate buffer, pH 7.5). The solution is agitated 15 seconds and then quenched by the addition of 0.01 ml of sodium metabisulfite solution (1.25 mg/ml in 0.5M sodium phosphate buffer, pH 7.5). A column prepared from Sephadex G-25 (Pharmacia Co.) is washed with 0.05M phosphate buffered saline, pH 7.5, 5% bovine serum albumin and then equilibrated with phosphate buffered saline. The iodination reaction mixture is applied to the column followed by PBS. Labeled protein is collected and diluted with bovine serum albumin to 5%.

B. Preparation of sample:

Male: Urine samples from males suspected of having contact with gonorrhea are prepared by centrifuging the first few milliliters of urine passed from the urethra. The supernatant solution is poured off and the remaining precipitate is suspended in 1 ml of phosphate buffered saline, 0.05M, pH 8.5.

Female: Vaginal washed are obtained as described in Example 3.

C. Diagnostic test

Radioactive IgAP (0.1 ml containing about 15,000 cpm) is added to 0.05 ml sample in 0.3 ml TRIS buffer, 0.05M, pH 8.0. The solution is contacted with inert beads with anti-serum to IgAP immobilized thereon for 1 hour at room temperature. The solution is centrifuged and the supernatant is monitored for radioactivity. Comparison to a standard curve gives quantitation of amount of IgAP in sample.

EXAMPLE 5

Detection of *Neisseria gonorrhea:* Radialimmunodiffusion

A. Preparation of reagents:

The antiserum to IgAP is prepared as described in Example 1. 0.5 mg antiserum in 1% softened agar with 0.05M phosphate buffered saline, pH 8.0, is poured into an Octolony disc plate and allowed to harden.

B. Preparation of sample—female

A tampon which has been inserted towards the cervix for 4–8 hours is removed to a receiving vessel containing 10 ml isotonic saline. The vessel is stoppered and shaken well to extract and lyse bacteria on the tampon.

C. Diagnostic Test 0.1 ml of sample are removed with a dropper to a central well in the Octolony disc. The disc is covered and stored at room temperature 2 hours after which it is observed for opacity. An opaque disc radiating from the central well indicates the presence of IgAP in the sample.

EXAMPLE 6

Extraction of and concentration of IgAP from a biological sample

A. Preparation of reagents

Antibody to IgAP is prepared and immobilized as given in Example 1.

B. Preparation of sample

Fluid biological samples including a vaginal wash, urine, extract of tampon or a swab, spinal fluid, synovial fluid or a bacterial culture are suitable. The sample may be lysed before extraction of IgAP, by addition of hypertonic salts followed by adjustment of pH back to 7.5 and ionic strength of about 0.05M for optimum conditions before treating sample with antibody.

C. Extraction of IgAP

To a 2 ml of biological sample is added 2 ml phosphate buffered saline (pH 7.5, 0.05M). The inert surface with anti-serum immobilized thereon is inserted into the sample and then removed and rinsed in PBS.

D. Concentration of IgAP

The moist surface with anti-serum-IgAP complex thereon is removed to a tube containing 1 ml or less of PBS at a pH lower than 6, prefferably about 5.0 and agitated thoroughly to break the antigen-antibody complex. IgAP is thereby caused to separate into solution.

EXAMPLE 7

Immunoassay of IgAP: Reaction with Chromophoric Substrate

A. Extraction of IgAP

IgAP is extracted froma biological sample by means of immobilized antibody to IgAP as described in Example 6.

B. Preparation of Substrate

IgAP, from human colostrum is prepared by the monoclonal hybridoma myeloma technique. IgAP is used to assay selectively the cell culture lines to insure production of pure substrate. The $IgA_1$ is tagged with dinitrophenyl hydrazine (DNP) by the method of Castner and Eisen (*J.A.C.S.* 75 4454 (1953).

C. Preparation of sample

Samples given in Examples 1 to 6 are suitable.

D. Diagnostic Test 5 ml of sample are contacted with inert paper strip with antibody to IgAP immobilized thereon. The strip with antibody-enzyme complex is then dropped into dialysis tubing (pore size 5000 A) containing phosphate buffered saline (PBS) (pH 8.0), 0.05M) and suspended in PBS of the same pH and ionic strength. After 2 hours the solution outside the tubing is inspected for color. The presence of color indicates the presence of IgAP.

EXAMPLE 8

Immunoassay of IgAP: Reaction with Chromophoric Immobilized Polypeptide

The procedure of Example 7 is followed but a polypeptide having a prolyl-threolyl bond is employed as chromogenic immobilized substrate.

EXAMPLES 9–15

Immunoassay with Monoclonal Antibody

Example 1, 3, 4, 5, 6, 7 and 8 may be performed with the monoclonal antibody replacing anti-serum or the globulin fraction in these examples.

EXAMPLES 16–29

The bacteria *Haemophilus influenza, Neisseria meningitidis* and *Streptococcus pneumoniae* may be detected in biological samples by the methods described in Examples 1, 3, 4, 5, 7, 8 and 9–15.

EXAMPLE 30

Diagnosis of gonorrhea: Immunoassay of IgAP in Extracts of the Uro-genital Membrane A. Preparation of Sample Samples are obtained by washes or extracted from swabs or tampons in the case of females. Samples in males are the first few milliliters of urine to be voided after a period of continence. Urethral exudate may also be used. Samples may be cultured on a medium selective for *Neisseria gonorrhea* and harvested prior to assay. Samples may also be lyzed to release enzyme into the extra-cellular environment. For example, lysozyme from egg white (Biozyme Laboratories) prepared in 0.03M TRIS buffer, pH 9.0 is incubated with 5 ml of sample at room temperature and then centrifuged to release lyzed enzyme into the supernatant fluid.

B. Immunoassay of IgAP

IgAP is assayed by its reaction with antibody by the techniques disclosed in Examples 1–29. Presence of IgAP in the uro-genital tract is presumptive evidence of gonorrhea. Further chemical tests establish the diagnosis positively.

EXAMPLE 31

Kit for Detection of Gonorrhea

A kit of apparatus and reagents for detection of gonorrhea is comprised of:

A. Sample collection device

In the case of males, a small vial for capture of the first few milliliters of urine to be washed from the urethra after a night of continence;

in the case of females, a tampon to be inserted in the vagina towards the cervix and worn in place during sleeping hours. A vial is included for receiving the worn tampon and washing the exudate therefrom.

B. The Antibody to IgAP

Packet 1: The antibody to IgAP is immobilized on a paper strip and hermetically packaged.

Packet 2: A second portion of antibody is tagged with 2,4-dinitro-benzene and sealed in sterile packet along with buffer salts and ionic salts.

C. Means for detecting reaction between sample and antibody

To a tube filled to a marked volume with water is added the contents of packet 1.

The paper strip from packet 2 is dipped into the sample, rinsed with buffer and dipped into tube containing contents of packet 1. The strip is removed, gently rinsed by dipping in buffer solution and inspected for color.

Color adhering to the strip indicates the presence of IgAP in the sample and is diagnostic of gonorrhea.

This kit may be applied by an individual for self-diagnosis of gonorrhea or may be used by a doctor in his office or clinic.

EXAMPLE 32

Kit for Diagnosis of Gonorrhea

A. Sample collection as described in Example 32.

B. Antibody to IgAP is embedded in gelatin in a Octolony type disc plate along with buffer and ionic salts as described in Example 5.

C. Means and method for detecting reaction between antibody and substrate.

A drop of sample is applied to the central well of the Octolony disc. The disc is covered and allowed to stand at room temperature for 4 hours after which it is inspected for opacity. A hazy white area irradiating from the central well indicates the presence of IgAP in the sample and hence gonorrhea.

This kit may be used for self-diagnosis or for professional diagnosis on individuals, or in a clinic for screening large numbers of samples.

EXAMPLE 33

Kit for detection of Gonorrhea

A. Sample collection as described in Example 29.

B. Antibody to IgAP immobilized on an inert strip in a hermetically sealed packet.

C. Means for detecting IgAP and antibody

IgA$_1$, tagged to 2,4-dinitrobenzene in a hermetically sealed packet along with isotonic buffer and salts.

D. Method

The inert strip with antibody to IgAP immobilized thereon is inserted into the sample and rinsed with buttered solution. Substrate IgA$_1$, along with buffering agent and salts is added to a tube and diluted to a marked volume. The contents of tube and sample are poured into a length of dialysis tubing sealed at one end as described in Example 7. After tubing is closed at the other end it is suspended in a solution of isotonic buffer and salts. Appearance of color in the suspending reaction solution outside the tubing proves the presence of IgAP in the sample and indicates gonorrhea. This kit may be used for self-diagnosis or professional diagnosis of gonorrhea.

What is claimed is:

1. Method of detecting *Neisseria, Haemophilus* or *Streptococcus* bacteria which elaborate the enzyme immunoglobulin A protease in a biological sample comprising:
   (a) contacting the biological sample with antibody which specifically binds to an antigenic site of the enzyme; and
   (b) detecting the resultant antibody-enzyme complex.

2. Method of claim 1 in which the bacteria detected are *Neisseria gonorrhea*.

3. Method of claim 1 in which the bacteria detected are selected from the group consisting of *Haemophilus influenza, Neisseria meningitidis* and *Streptococcus pneumoniae*.

4. Method of claim 1 wherein said sample is a biological fluid or a membrane extract.

5. Method of claim 4 wherein said biological fluid or membrane extract is maintained under conditions suitable for growth of bacteria to be detected prior to contact with said antibody.

6. Method of claim 4 wherein the biological fluid or membrane extract is treated with a suitable lysing agent prior to contact with said antibody.

7. Method of claim 1 wherein said antibody is immobilized on an inert support.

8. Method of claim 7 wherein the immobilized complex is separated from said sample and contacted with a second antibody which specifically binds to an antigenic site of the enzyme IgAP under conditions suitable for forming an immobilized antibody-IgAP-antibody complex, said second antibody being labelled with a chromophoric or radioactive group.

9. The method of claim 1 wherein said antibody is suspended in a gelatinous medium containing buffers and ionic salts suitable for aiding formation of the antibody-enzyme complex and wherein said sample is applied to a portion of said gelatinous medium.

10. Method of claim 1 wherein said antibody-enzyme complex is detected by radioimmunoassay.

11. Method of claim 10 wherein IgAP is conjugated with a radioactive element and the antibody which specifically binds to an antigenic site of the enzyme IgAP is immobilized on an inert support.

12. The method of claim 1 wherein said assay is enzyme linked immunoassay.

13. The method of claim 1 wherein said sample is contacted with latex beads coated with the antiserum to IgAP, said beads being suspended in albumin, and the agglutination thereof is determined.

14. Method of claim 1 wherein said antibody-enzyme complex is detected by an assay selected from the group consisting of radialimmunodiffusion, bidentate ligand binding, enzyme linked immunoassay, radioimmunoassay and haemagglutination.

15. The method of claim 1 including the step of contacting substrate for IgAP with IgAP which has been isolated from said sample by means of immobilized antibody to IgAP.

16. The method of claim 15 wherein said substrate is IgA$_1$, or a polypeptide containing a prolyl-threonyl bonding pair.

17. Screening test for gonorrhea comprising the step of conducting an immunoassay of a biological sample by contacting said sample with antibody which specifically binds to an antigenic site of the enzyme IgAP elaborated by Neisseria gonorrhea and detecting the resultant complex formation.

18. Reagent useful in the immunoassay of the enzyme IgAP comprising an antibody which specifically binds to an antigenic site of the enzyme IgAP.

19. A composition comprising the antibody of claim 18 in a reaction medium of pH and ionic strength suitable for formation of an immune complex between IgAP and said antibody.

20. The antibody of claim 18, said antibody being immobilized on an inert support.

21. The antibody of claim 18, said antibody being conjugated with a chromophoric molecule or labelled with a radioactive element.

22. Kit for the detection of *Neisseria gonorrhea* comprising, in packaged combination:
   (a) a first container containing an antibody which specifically binds to an antigenic site of the enzyme IgAP; and
   (b) a second container containing a reagent for detecting reaction between a biological sample and the antibody.

23. Kit of claim 22, wherein siad antibody is immobilized on an inert support.

24. Kit of claim 22, wherein said antibody is conjugated with a chromophore, enzochromophore, fluorophore, luminophore or a radioactive element.

25. Kit of claim 22 additionally containing reagents for reaction solution comprising buffer and ionic salts.

26. Kit of claim 22, wherein said reagent for detecting said reaction comprises a gelatinous medium in which antibody which specifically binds to an antigenic site of the enzyme IgAP is suspended.

27. Kit of claim 22, wherein said reagent for detecting said reaction comprises substrate of the enzyme IgAP.

28. Kit of claim 27 wherein said substrate is labelled with a chromophore or a radioactive element.

29. Kit of claim 22 comprising in addition reagents for lysing cells in the sample.

30. Kit of claim 22 comprising in addition a sample collector.

31. Kit of claim 30 wherein said sample collector comprises a urine collector, a tampon or a swab or any combination thereof.

* * * * *

UNITED STATES PATENT AND TRADEMARK OFFICE
CERTIFICATE OF CORRECTION

PATENT NO. : 4,582,699

DATED : April 15, 1986

INVENTOR(S) : Kittie A. Murray

It is certified that error appears in the above-identified patent and that said Letters Patent is hereby corrected as shown below:

On the title page:
Please change spelling of Assignee from Magbon to

-- Mabgon Test Company --

*Signed and Sealed this*

*Fifth* Day of *August 1986*

[SEAL]

*Attest:*

DONALD J. QUIGG

*Attesting Officer*    *Commissioner of Patents and Trademarks*